(12) United States Patent
Bernard

(10) Patent No.: US 12,310,772 B2
(45) Date of Patent: May 27, 2025

(54) RADIOLOGY DEVICE WITH SEVERAL SOURCES OF IONIZING RAYS AND METHOD IMPLEMENTING THE DEVICE

(71) Applicant: THALES, Courbevoie (FR)

(72) Inventor: Guillaume Bernard, Moirans (FR)

(73) Assignee: THALES, Courbevoie (FR)

( * ) Notice: Subject to any disclaimer, the term of this patent is extended or adjusted under 35 U.S.C. 154(b) by 0 days.

(21) Appl. No.: 17/769,289

(22) PCT Filed: Oct. 19, 2020

(86) PCT No.: PCT/EP2020/079345
§ 371 (c)(1),
(2) Date: Apr. 14, 2022

(87) PCT Pub. No.: WO2021/074445
PCT Pub. Date: Apr. 22, 2021

(65) Prior Publication Data
US 2024/0138785 A1    May 2, 2024

(30) Foreign Application Priority Data
Oct. 17, 2019   (FR) ........................................ 1911595

(51) Int. Cl.
*A61B 6/40* (2024.01)
*A61B 6/00* (2006.01)
*A61B 6/03* (2006.01)

(52) U.S. Cl.
CPC ............ *A61B 6/4007* (2013.01); *A61B 6/032* (2013.01); *A61B 6/4078* (2013.01); *A61B 6/4435* (2013.01); *A61B 6/5205* (2013.01)

(58) Field of Classification Search
CPC ..... A61B 6/4007; A61B 6/032; A61B 6/4078; A61B 6/4435; A61B 6/5205
See application file for complete search history.

(56) References Cited

U.S. PATENT DOCUMENTS 4,239,972 A * 12/1980 Wagner ................ G01N 23/083
378/10
6,229,870 B1   5/2001 Morgan
(Continued)

FOREIGN PATENT DOCUMENTS

| CN | 102928510 A | 2/2013 |
| EP | 1 378 113 B1 | 5/2011 |

(Continued)

OTHER PUBLICATIONS

Giudiceandrea, et al., "A high speed CT scanner for the sawmill industry", 17th International Nondestructive Testing and Evaluation of Wood Sympoisium, 2011.
(Continued)

*Primary Examiner* — David P Porta
*Assistant Examiner* — Mamadou Faye
(74) *Attorney, Agent, or Firm* — BakerHostetler

(57) ABSTRACT

A radiology device includes an ionizing ray generator and a detector configured to detect the rays emitted by the generator, the generator and the detector being opposite with respect to one another, the device delimiting a useful volume, passed through by the ionizing rays from the generator and received by the detector, the generator comprising several sources distributed along a direction and each emitting a beam of ionizing rays that is essentially flat and of fantail form, the sources being disposed so as to irradiate all of the useful volume without translation. A method is provided implementing a device and consisting in successively sequencing the emission of several of the sources.

16 Claims, 4 Drawing Sheets

(56) References Cited

U.S. PATENT DOCUMENTS

| | | | |
|---|---|---|---|
| 7,396,162 B1 | 7/2008 | Edic et al. | |
| 2004/0213380 A1* | 10/2004 | Shaw | A61B 6/06 378/145 |
| 2004/0264628 A1* | 12/2004 | Besson | G21K 1/10 378/5 |
| 2006/0008047 A1* | 1/2006 | Zhou | G01N 23/046 378/10 |
| 2010/0266097 A1 | 10/2010 | Okunuki et al. | |
| 2017/0287173 A1 | 10/2017 | Zhang et al. | |
| 2019/0206652 A1* | 7/2019 | Akinwande | G01N 23/041 |
| 2019/0261930 A1* | 8/2019 | Wang | A61B 6/4014 |
| 2021/0212189 A1* | 7/2021 | Gonzales | H05G 1/32 |

FOREIGN PATENT DOCUMENTS

| | | | |
|---|---|---|---|
| JP | 2000-175895 A | 6/2000 | |
| JP | 2010-505454 A | 2/2010 | |
| JP | 2010-069012 A | 4/2010 | |
| JP | 2014-050737 A | 3/2014 | |
| JP | 2017-185219 A | 10/2017 | |
| WO | 2019/011980 A1 | 1/2019 | |

OTHER PUBLICATIONS

Notification of Reason(s) for Refusal issued in Japanese Patent Application No. 2022-522903 dated Apr. 23, 2024, with English translation.

* cited by examiner

RADIOLOGY DEVICE WITH SEVERAL SOURCES OF IONIZING RAYS AND METHOD IMPLEMENTING THE DEVICE

CROSS-REFERENCE TO RELATED APPLICATIONS

This application is a National Stage of International patent application PCT/EP2020/079345, filed on Oct. 19, 2020, which claims priority to foreign French patent application No. FR 1911595, filed on Oct. 17, 2019, the disclosures of which are incorporated by reference in their entirety.

FIELD OF THE INVENTION

The invention relates to a radiology device and a method implementing the device. The invention can be implemented in the medical field, in industry for conducting non-destructive inspections and in security for detecting dangerous objects or materials. The invention relates also to a method implementing the radiology device. The invention is of particular use in computer tomography. The invention can also be implemented in conventional radiology without movement around the object to be x-rayed.

BACKGROUND

As is known, computer tomography, also called scenography, implements a system equipped with an x-ray tube emitting a fantail-form collimated beam, known as "fan beam", associated with a bar detector disposed opposite the beam. The tube and the detector revolve around a table accommodating the patient. On each revolution, the table advances along the axis of rotation of the tube and of the detector. Computer processing allows 2D cuts or 3D volumes of the anatomical structures of the patient to be reconstructed. This system is known as "CT-scanner", "CT" being the acronym for "computer tomography".

More recently, other systems having a tube emitting a conical x-ray beam, known as "cone beam", associated with a flat detector, have emerged. The tube and the detector are mounted on a revolving arm in the form of the letter C. These systems are called "C-arm" or are known by the acronym CBCT, for "cone beam computer tomography". The conical form of the beam makes it possible to dispense with the translation implemented for the CT-scanner. For CBCT, the acquisition of the data is much faster because it requires only a single revolution around the patient of the assembly formed by the tube and the detector.

In the systems of CT-scanner type, the flat form of the beam associated with the bar detector makes it possible to limit the effects of scattered radiation notably by Compton interactions of the x-rays with the patient. In the systems of CBCT type implementing a conical beam associated with a flat detector, it is possible to minimize the effects of the scattered radiation by using an anti-scatter grid placed on the detector. However, the CBCT type systems do not make it possible to obtain an adequate definition for certain medical examinations, notably for the analysis of soft tissues.

Moreover, in the known systems, of CT-scanner or CBCT type, the x-ray tubes have significant dimensions, notably because of the implementation of thermionic cathodes. Furthermore, depending on the power of the x-ray tubes, the latter may be equipped either with a fixed anode or with a revolving anode allowing a spreading of the dissipated thermal power. The fixed anode tubes have a power of a few kilowatts and are notably used in low power medical, security and industrial applications. The revolving anode tubes can exceed 100 kilowatts and are primarily implemented in the medical field for imaging requiring significant x-ray fluxes making it possible to enhance the contrast of the images obtained. As an example, the diameter of an industrial tube is of the order of 150 mm at 450 kV, 100 mm at 220 kV and 80 mm at 160 kV. The voltage indicated corresponds to the potential difference applied between the cathode and the anode.

SUMMARY OF THE INVENTION

The invention aims to produce a radiology device combining the advantages of the two known device types, CT-scanner and CBCT, while avoiding the drawbacks thereof. A device according to the invention comprises a generator and a detector revolving together around the patient or more generally the object to be x-rayed. It implements beams of "fan beam" type while requiring only a single revolution, or even a fraction of a revolution, around the object to be x-rayed.

The objective of the invention is to produce a radiology device that has a much more lightweight mechanical structure than that of a CT-scanner type device while retaining a low susceptibility to the effects of scattered radiation. In certain variants of the invention, it is even possible to correct the effects of the scattered radiation and thus clearly enhance the quality of the radiological images obtained, both for two-dimensional images and for three-dimensional images.

To this end, the subject of the invention is a radiology device comprising an ionizing ray generator and a detector configured to detect the rays emitted by the generator, the generator and the detector being opposite with respect to one another, the device delimiting a useful volume, passed through by the ionizing rays from the generator and received by the detector, the generator comprising several sources distributed along a direction and each emitting a beam of ionizing rays that is essentially flat and of fantail form toward the detector (14), the sources being disposed so as to irradiate all of the useful volume without translation. The device further comprises a computer configured to produce a two-dimensional image of an object to be x-rayed situated in the useful volume without relative movement between the generator and the detector, the computer being configured to collect information from the detector along bands of the detector, each band being disposed opposite one of the beams and to establish the two-dimensional image by juxtaposing the information from the different bands of the detector.

Advantageously, the computer is configured to produce an estimation of the radiation scattered in each of the bands as a function of radiation measured by the detector outside of the band concerned and to subtract the estimation of the scattered radiation from the measurements performed by the detector in the band concerned.

Advantageously, the computer is configured to produce an estimation of the radiation scattered in each of the bands as a function of a model of decreasing scattered radiation moving away from the band concerned (**14-*i***).

Advantageously, the device comprises a support capable of bearing an object to be x-rayed and an actuator making it possible to move an assembly formed by the generator and the detector around the support. The computer can then be configured to produce a three-dimensional image of an object to be x-rayed situated in the useful volume from several two-dimensional images produced by moving, between each two-dimensional image, the assembly formed by the generator and the detector around the support.

Advantageously, the detector is formed by a flat panel extending on two right-angled axes, a first of the two axes being parallel to the direction in which the sources are distributed, a second of the two axes belonging to a plane in which one of the beams is propagated.

Advantageously, planes in which the beams are propagated are parallel to one another.

Advantageously, each source comprises a cold cathode emitting an electron beam by field effect.

Advantageously, at least several of the sources have a common vacuum chamber.

As a variant, the generator can comprise several series of aligned sources, each series being aligned along a direction and each emitting an essentially flat beam of ionizing rays, the planes of each of the beams being parallel to one another.

The directions of each of the series of sources can be parallel to one another.

Also a subject of the invention is a method implementing a device according to the invention, consisting in successively sequencing the emission of several of the sources.

The sources are ordered along their direction and advantageously grouped together in subsets each grouping together evenly distributed sources, the subsets being nested in one another, the method then consisting of controlling the simultaneous emission of the sources of the same subset and in successively sequencing the emission of the different subsets.

Advantageously, the method consists in spatially and temporarily synchronizing the sources and the detector.

Advantageously, the method consists in synchronizing the emission of each source with an allocation of the corresponding band of the detector.

Advantageously, the method consists in synchronizing the emission of each source with an allocation of the corresponding band of the detector.

Advantageously, the method consists in combining the emission of the different sources and the movement of the actuator.

Advantageously, the method consists in moving the actuator continuously during the emission of the different sources.

BRIEF DESCRIPTION OF THE DRAWINGS

The invention will be better understood and other advantages will become apparent on reading the detailed description of an embodiment given by way of example, the description being illustrated by the attached drawing in which.

In the interests of clarity, the same elements will bear the same references in the various figures.

DETAILED DESCRIPTION

Figures 1A, 1B:
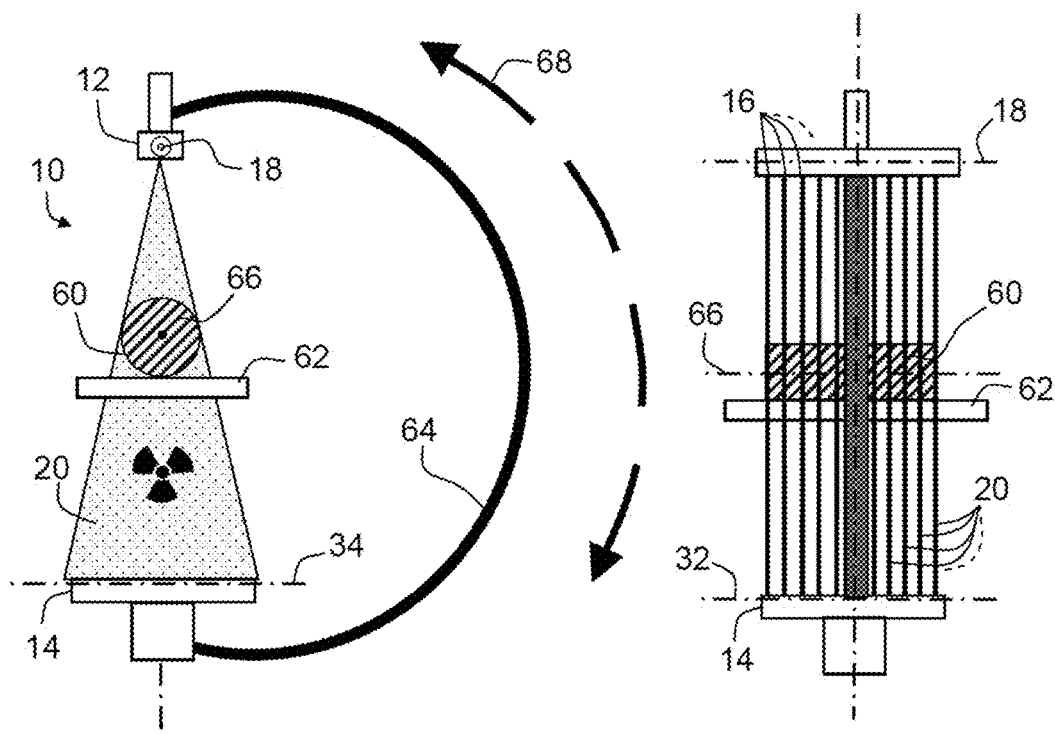
FIGS. 1a and 1b illustrate, by front and profile views, a first variant of a radiology device according to the invention.

FIGS. 1a and 1b schematically illustrate the main components of a radiology device 10 used for computer tomography examinations. The device 10 is of particular use in medical examinations. It is of course possible to implement the device 10 in any other field, notably in industry for conducting non-destructive inspections and in security for detecting dangerous objects or materials.

The device 10 comprises an ionizing ray generator 12 and a detector 14 configured to detect the rays emitted by the generator 12. The object to be x-rayed is placed between the generator 12 and the detector 14 on a support 62. The device 10 also comprises computing means, not represented and that make it possible to process the data from the detector 14 in order to make them usable for an operator of the device. This processing can notably produce a 2D or 3D reconstruction of the object to be x-rayed.

The generator 12 and the detector 14 are opposite with respect to one another. In a simple embodiment of the radiology device, the generator 12 and the detector 14 can be fixed with respect to one another. Alternatively, it is possible to provide a radiology device in which the generator 12 and/or the detector 14 are movable with respect to one another. Hereinbelow, it will be considered that they are fixed with respect to one another.

The generator 12 comprises several ionizing ray sources 16 distributed along a direction 18. Each source 16 emits a beam 20 of ionizing rays that is essentially flat and of fantail form. This type of beam is known in the literature as "fan beam". In a simple configuration, the direction 18 is rectilinear and the planes in which the beams 20 are propagated are essentially parallel to one another and at right angles to the direction 18. Other configurations are possible in the context of the invention. The direction 18 can be curved and the planes of the beams 20 can be neither parallel to one another nor at right angles to the direction 18.

The sources 16 are advantageously compact, as for example described in the patent application published under the number: WO 2019/011980 A1 filed in the name of the applicant. Each source comprises, in a vacuum chamber, a cathode emitting an electron beam, an anode having a target bombarded by the electron beam and emitting a beam of ionizing rays. The cathode advantageously emits the electron beam by field effect toward the target. This type of cathode is also known as cold cathode, unlike the hot cathodes that are also called thermionic cathodes.

The benefit of implementing compact cold cathode sources is to allow the convergence of their focus point along the direction 18.

Figure 2:
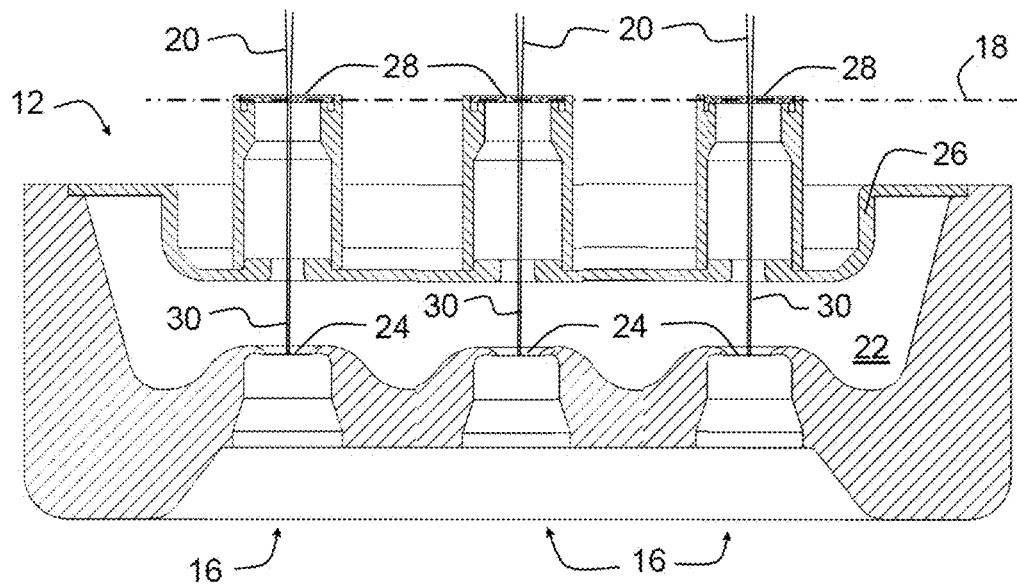
FIG. 2 represents an example of an ionizing ray generator that can be implemented in a radiology device according to the invention.

FIG. 2 represents in more detail an example of generator 12 in which several of the sources 16 have a common vacuum chamber 22. It is notably possible to produce all the sources 16, or at least several of them, in a single vacuum chamber 22. The benefit of a vacuum chamber common to several sources 16 is to allow the convergence of the focusing points of the beams 20. The distribution of the sources 16 along the direction 18 can be uniform as represented in FIG. 2 in which the distance separating two adjacent sources 16 is constant. It is also possible to opt for a non-uniform distribution. Alternatively, in the context of the invention, it is of course possible to implement one vacuum chamber for each source 16.

In FIG. 2, the cold cathodes 24 are distributed along the axis 18. The sources 16 can comprise an anode 26 common to the different sources 16. The anode 26 bears as many targets 28 as there are cathodes 24. Each cathode 24 emits an electron beam 30 toward the target 28 which is associated with it. The interaction between an electron beam 30 and a target 28 makes it possible to generate a beam 20 of ionizing rays. The different sources 16 can be controlled independently of one another by means of control of their respective cathode 24.

It is clearly understood that the invention can also be implemented with thermionic cathode sources.

The detector 14 is configured to receive the different beams 20 emitted by the sources 16. The detector 14 can comprise several individual bar detectors. Each individual detector is disposed opposite one of the beams 20. Alternatively, the detector 14 is produced in the form of a surface detector which can be curved or in the form of a flat panel extending on two right-angled axes 32 and 34. The axis 32 is parallel to the direction 18 and the axis 34 belongs to one of the planes of the beams 20. A flat panel is for example described in the European patent EP 1 378 113 filed by the company TRIXELL. This patent addresses the butt-joining of several substrates in order to produce a flat panel of dimensions greater than those of the standard substrates. Other detectors produced in the form of flat panels and produced by the company TRIXELL or by other companies can also be implemented in the context of the invention.

The use of a flat panel simplifies the capturing of the data from the detector 14. In fact, the flat panel can be equipped with reading circuits and a multiplexer, the output of which delivers all of the data from the detector 14 over a serial link.

Figure 3:
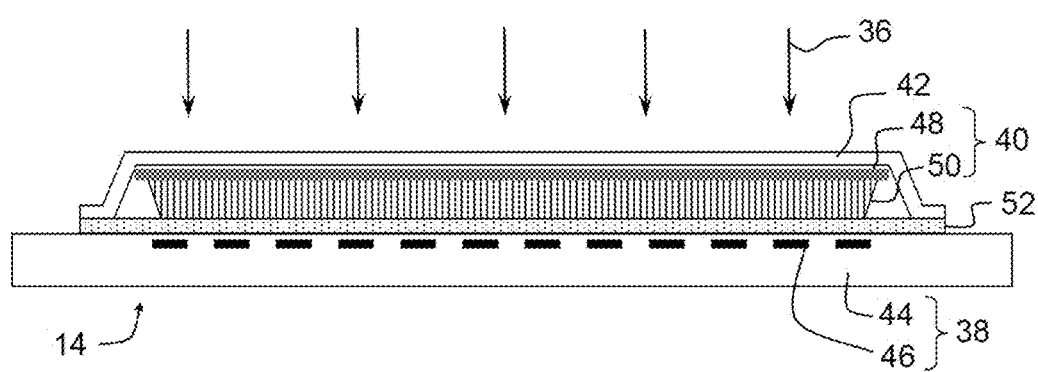
FIG. 3 represents, in cross section, an example of a detector in flat panel form that can be implemented in a radiology device according to the invention.

FIG. 3 represents, in cross section, an example of detector 14 in flat panel form. The detector 14 allows the detection of ionizing rays, the direction of which is shown by the arrows 36 belonging to the different planes of the beams 20. The detector 14 comprises a sensor 38, a scintillator 40 transforming the ionizing rays into radiation to which the sensor 38 is sensitive, for example in the visible band, and a rigid input window 42 that is passed through by the ionizing rays upstream of the scintillator 40. It is possible to dispense with the scintillator by implementing a sensor that is directly sensitive to the ionizing rays. The scintillator 40 is disposed between the sensor 38 and the input window 42. The sensor 38 comprises a substrate 44 and photosensitive elements 46 disposed on the substrate 44. The scintillator 40 comprises a support 48 and a scintillating substance 50 disposed on the support 48. Alternatively, it is possible to dispense with the support 48 and to deposit the scintillating substance 50 directly on the sensor 38. A tight sealing joint 52 fixes the input window 42 to the substrate 44. The sealing joint 52 can be used to fix the scintillator 40 to the sensor 38. The photosensitive elements 46 are organized in rows and columns. The rows extend along the axis 32 and the columns extend along the axis 34, or vice versa.

In FIG. 1b, the different beams 20 of ionizing rays are represented at a distance from one another, parallel to one another, each in a plane at right angles to the direction 18. In practice, in order for the object to be x-rayed to be completely traversed by the ionizing rays, the beams 20 are contiguous, even overlap slightly. More specifically, the device 10 delimits a useful volume 60, identified in FIG. 1a, in which the object can be x-rayed, that is to say passed through by ionizing rays received by the detector 14. The beams 20 can flare out around their median plane represented vertically in FIG. 1b to become contiguous, even overlap within the useful volume 60. Along their direction 18, the sources 16 are disposed so as to irradiate all of the useful volume 60 without translation, contrary to the radiology devices of CT-scanner type which require the translation of the object to be x-rayed with respect to the assembly formed by the x-ray generator and the associated detector to scan their useful volume.

The device 10 comprises a support 62 capable of bearing the object to be x-rayed. In the medical field, the support 62 is, for example, a table on which a patient can lie down. To perform a computer tomography examination, the assembly formed by the generator 12 and the detector 14 revolves around the support 62. The generator 12 and the detector 14 can be linked by an arm 64, for example in the form of a circular arc centered on the axis 66 of rotation of the generator 12 and of the detector 14. The axis of rotation 66 is at right angles to the different planes of the beams 20. To perform the rotation, the device comprises an actuator represented by a rotation movement 68. During the rotation, the beams 20 revolve around the axis 66. Consequently, the useful volume 60 in which, for all the rotation phases, with the beams 20 producing irradiation and reaching the detector 14, is of cylindrical form about the axis 66. As an example, it is possible to obtain a useful volume 60 of 10 cm along the axis 66 by means of a generator 12 comprising 10 or so sources 16 regularly distributed along the direction 18 which, here, is rectilinear. A generator 12 comprising 10 sources 16 distributed every centimeter can be produced, as represented in FIG. 2, with a common vacuum chamber 22. In practice, the invention is advantageously implemented for a generator 12 comprising at least 10 sources 16 in order to obtain a useful volume of advantageous minimum size.

For reasons of production of the common vacuum chamber 22, the latter may not be able to exceed a maximum number of sources 16, for example 10 sources 16. If a device having more than 10 sources is desired to be produced, it is possible to produce a generator 12 having several vacuum chambers, the sources 16 of which are disposed in alignment with one another in the direction 18. It is also possible to slightly offset the directions 18 of the different vacuum chambers while keeping them parallel to one another.

The actuator can be a rotary motor driving the arm 64 about the axis 66. Alternatively, the actuator can generate a more complex movement produced from a combination of translations and rotations. This movement can make it possible to modify the form or the position of the useful volume. In computer tomography, in order to ensure a good reconstruction, it is important for the object to be x-rayed to be traversed in all directions by ionizing radiation, in order to observe the Tuy condition. A complex movement of the actuator can make it possible to observe this condition in a volume that does not have a circular section as represented in FIGS. 1a and 1b. That makes it possible to better adapt to the form of the object to be x-rayed. The movement is advantageously contained in the plane of FIG. 1b, that is to say in a plane at right angles to the planes of the beams 20. To perform a computer tomography examination, with a device according to the invention, it is not necessary for the movement produced by the actuator to include a translation at right angles to the planes of the beams 20 as with a device of CT-scanner type. However, a translational movement at right angles to the planes of the beams 20 can be useful in order to increase the length of the useful volume 60 along the axis 66.

Figure 4:
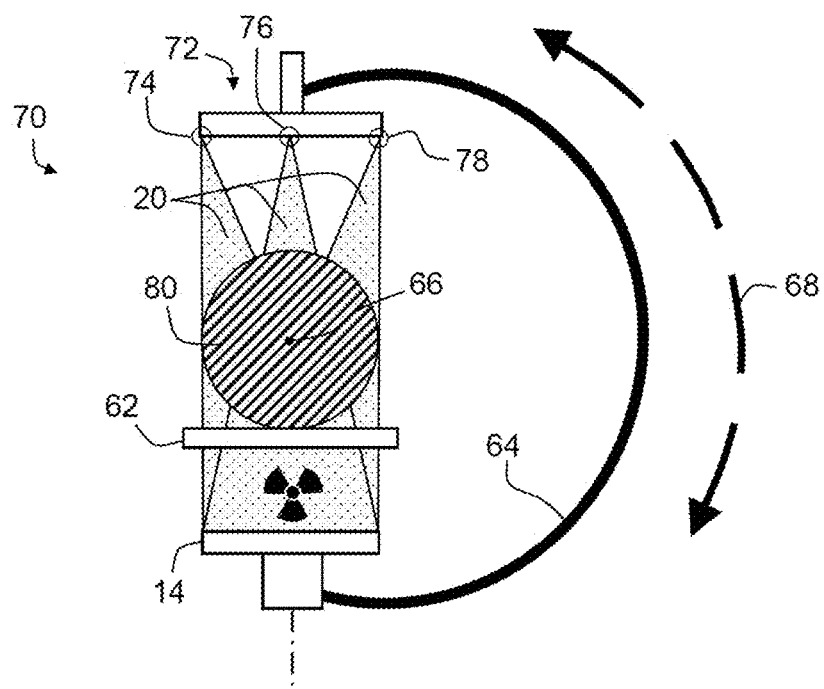
FIG. 4 illustrates, by a front view, a second variant of a radiology device according to the invention.

FIG. 4 illustrates a second variant of a radiology device 70 according to the invention that allows the useful volume to be enlarged. Once again, there are the detector 14, the support 62, the arm 64 and the actuator 68. The device 70 comprises a generator 72 which differs from the generator 12 by the presence of several series of sources 16. In practice, the generator 12 comprises only a single series of sources 16 aligned along the direction 18. The different series of the generator 72 are each aligned along a direction. In the example represented, the generator 72 comprises three series of sources, respectively aligned on directions 74, 76 and 78. It is of course possible to implement this variant for other numbers of series. As previously, the different sources 16 of the generator 72 each emit an essentially flat beam 20 of ionizing rays, the planes of each of the beams 20 being, for example, parallel to one another. FIG. 4 is represented in cross section in a plane at right angles to the axis 66. The cross section of the useful zone 80 is, here, a disk. The directions 74, 76 and 78 can be parallel to one another, and parallel to the axis of rotation 66. In this case, the useful volume 80 extends cylindrically about the axis 66. Other dispositions of the directions 74, 76 and 78 are also possible, for example parallel to one another and not parallel to the axis 66, or even not parallel to one another. These alternatives make it possible to adapt the form of the useful zone 80 as required.

In the two variant devices 10 and 70 described previously, the simultaneous emission of all the sources 16 can lead to difficulties in discriminating, at the output of the detector 14, the photons from each source 16. This discrimination is notably useful for limiting the scattered radiation effects. These effects can be limited by placing, on the detector 14, an anti-scatter grid. One alternative, that can be combined with the presence of an anti-scatter grid, consists in successively sequencing the emission of several of the sources 16. The aim of this sequencing is to avoid the simultaneous emission of several sources 16 from which the respective scatter radiation can be added together. In other words, it is possible to emit only with one of the sources 16 at a time or else allow the simultaneous emission of sources 16 that are sufficiently far apart from one another according to the gradient of decay of the halo created by the scattered radiation. When it is desired to irradiate all of the useful volume 60 or 80, all the sources 16 must emit at least once. It is also possible to reduce the length of the useful volume along the axis 66, for example when the object to be x-rayed is smaller than the maximum useful volume of the device. This reduction of the useful volume is done by selecting a part of the sources 16, parts situated opposite the object to be x-rayed.

Figure 5A:
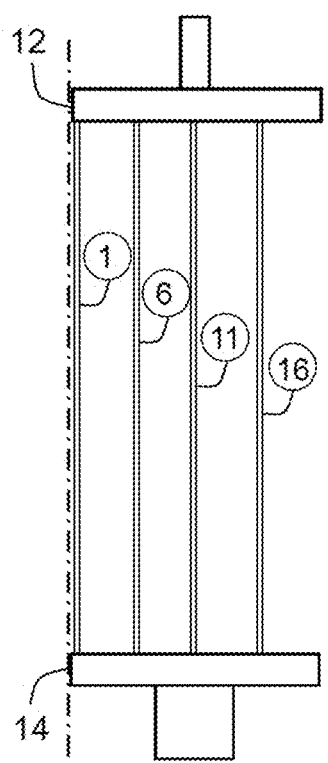
FIGS. 5a, 5b and 5c illustrate a method implementing a device according to the invention.
Figure 5B:
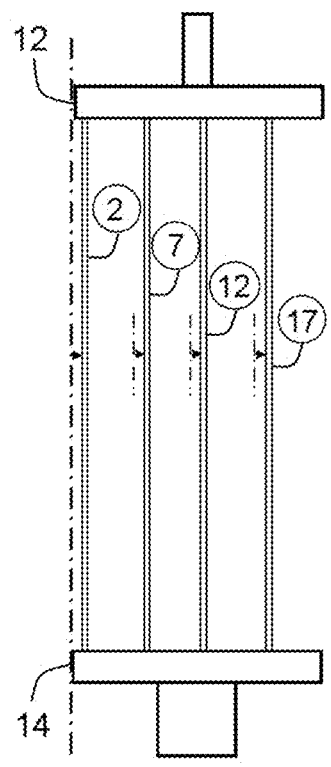
Figure 5C:
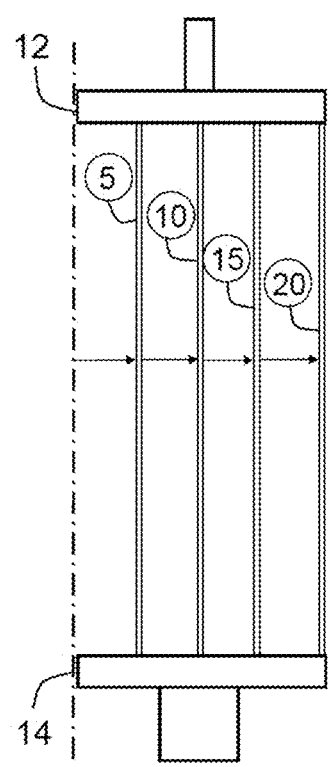

FIGS. 5a to 5c illustrate this sequencing of simultaneous emissions in which, at each emission instant, the separation between two sources 16, along the direction 18, is retained. The sources 16 are grouped together in several subsets each grouping together evenly distributed sources. The subsets are nested in one another and the method consists in controlling the simultaneous emission of the sources 16 of the same subset and in successively sequencing the emission of the different subsets.

More specifically, the generator 12 comprises N sources 16 that are ordered in the direction 18. The rank of a source 16 is denoted i, i therefore varying from 1 to N. The distance along the direction 18 separating two successive sources 16 i and i+1 is constant for the N sources 16. The sources are divided up into P subsets each comprising the sources of rank j.(N/P+1)+i, j varying from 0 to N/P−1 for one subset and i varying from 1 to P for each subset, i and j being natural integers. The subsets emit in turn. It is not obligatory for N to be divisible by P. If N is not divisible by P, in the formula giving the rank, the integer part of N/P will be taken and the sources of ranks higher than integer part (N/P).P are then divided up into the subsets by retaining the same pitch between sources 16.

In FIGS. 5a to 5c, the rank of the sources 16 is specified. In FIG. 5a, at the first instant of the cycle, the sources of rank 1, 6, 11 and 16 emit. At the next instant, represented in FIG. 5b, the sources of rank 2, 7, 12 and 17 emit. At the last instant of the cycle, represented in FIG. 5c, the sources of rank 5, 10, 15 and 20 emit. In this example, the emission cycle of the different subsets sequences the emissions in the order of the rank of the first source of each subset. It is also possible to have the subsets emit in other orders, for example by first of all having the subsets in which the first source has an odd rank emit first followed by the subsets in which the first source has an even rank. That makes it possible to limit the remanence in the reading done by the detector 14.

The successive emissions performed by the different sources, whether that emission is individual, one source at a time, or collective, that is to say per subset, can also be implemented with the device 70, in which it is also advantageous not to have sources that are too close to one another emitting simultaneously. In the case of emissions by subsets, each of them can comprise sources belonging to the same direction or to different directions.

Complementing the successive emissions, it is advantageous to synchronize the detector to them. More specifically, as indicated above, the detector 14 comprises photosensitive elements organized in a matrix of rows and columns. The row and column designation is purely conventional, so, hereinbelow, the term row will be used, but may be applied either to a row or a column. The detector sequences an acquisition phase followed by a matrix reading phase. The reading can be done row by row. By orienting the detector 14 in such a way that the orientation of the reading rows coincides with the orientation of the planes of the beams 20, it is possible to perform the reading only of the row or rows closest to the plane of the beam 20, and more specifically the rows illuminated by the beam or beams 20 emitting simultaneously. Thus, the ionizing rays deflected by the object to be x-rayed, essentially forming the scattered radiation, can be disregarded when reading the matrix. More generally, the sources 16 and the detector 14 are spatially and temporarily synchronized.

In computer tomography, it is necessary to rotate the generator 12 or 72 and the detector 14 in order to produce a 2D or 3D reconstruction of the object to be x-rayed. The presence of several sources 16 emitting parallel beams makes it possible to perform only a single revolution, or only a fraction of a revolution, to obtain the different cuts necessary to the reconstruction. To this end, the emission of the different sources 16 and the rotation of the actuator 68 are combined. Different combination modes are possible. It is for example possible to have the actuator 68 revolving incrementally and to have all the sources 16 emit successively between each rotation increment. It is also possible to perform smaller increments and perform an emission of one source 16 or a subset of sources 16 between each increment. It is also possible to have the actuator 68 revolving continuously and, during its rotation, perform as many emission cycles as necessary. In practice, during a continuous rotation, it is possible to consider that, during an emission, the actuator 68 is virtually static. The continuous movement of the arm 64 bearing the detector 14 and the generator 12 or 72 makes it possible to limit the effects of the mechanical inertia of the movable elements. In fact, in the case of incremental movement of the actuator, each stop and each start of the actuator generates jerks degrading the accuracy of the positioning of the arm 64. The continuous movement of the actuator 68 makes it possible to limit these jerks. Preferably, the continuous movement of the actuator 68 is done uniformly, that is to say at constant speed, which completely eliminates all the jerks. At the same time, while retaining a continuous movement of the actuator 68, it is possible to slow down its movement during each emission of a source 16 and to speed it up between two emissions.

It is also possible to implement a device according to the invention that does not have an actuator. In other words, the generator 12 or 72 and the detector 14 remain fixed with respect to the support 62. This device is useful for x-raying objects that can generate strong scattering by Compton interaction, for example in the medical field for performing a pulmonary x-ray. This type of radiology is generally performed by means of a generator emitting a conical x-ray beam. The generator is associated with a flat detector in which the scattered radiation can be discriminated from the useful information only with an anti-scatter grid; a grid whose effectiveness is middling and imposes a greater dose of ionizing rays on the patient. By implementing the invention, it is possible to emit successively by the different sources 16. By temporarily and spatially synchronizing the detector 14 and the generator 12 or 72, it is possible to avoid the detection of scattered radiation. In practice, a complete emission cycle by all the sources of the device can be sufficiently fast to be considered instantaneous and thus obtain a virtually instantaneous image of the object to be x-rayed.

Figure 6:
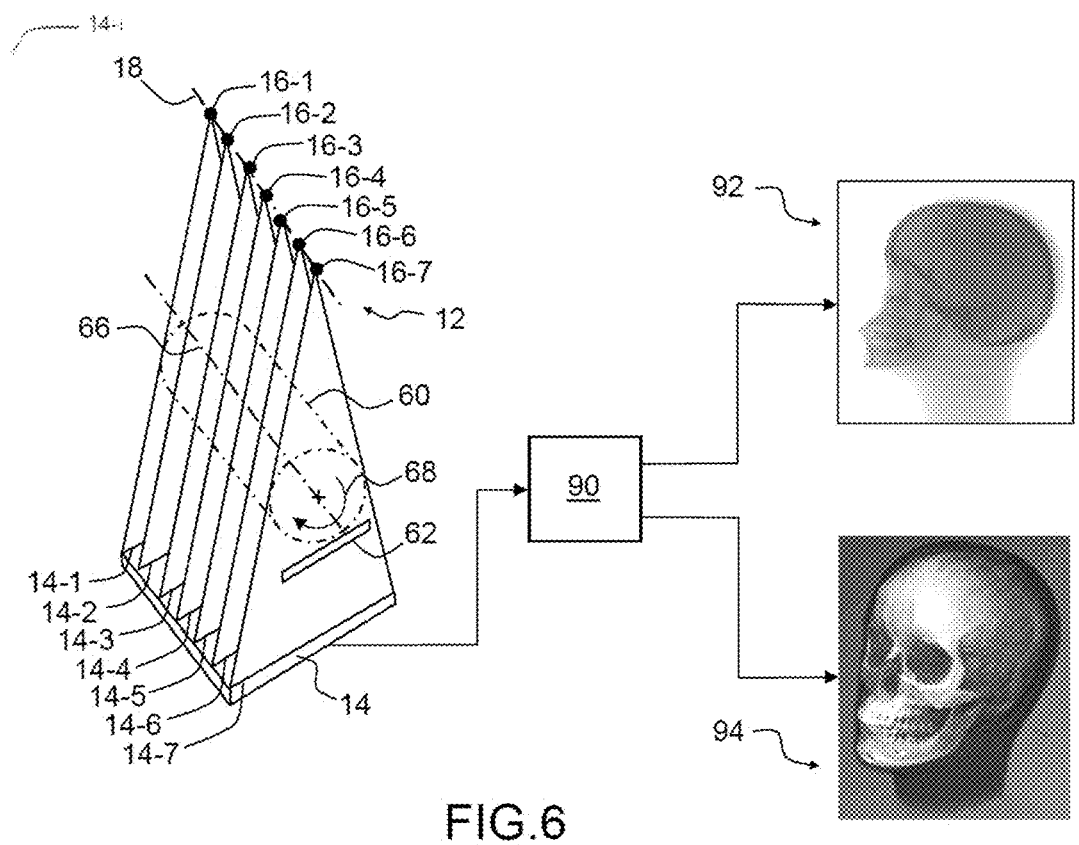
FIG. 6 illustrates other components of the radiology device.

FIG. 6 again represents the radiology device 10 to illustrate the means allowing it to produce an image. The device comprises a computer 90 configured to produce a two-dimensional image 92 of an object to be x-rayed situated within the useful volume 60. Each source, here identified 16-1 to 16-7, emits a beam 20 toward the detector 14. As described above, the emissions of the different sources 16-1 to 16-7 are advantageously performed sequentially. Each beam 20 is received by a region of the detector 14, forming a band of pixels of the detector 14 disposed opposite each beam 20. The bands are identified 14-1 to 14-7 with reference to the sources 16-1 to 16-7 opposite.

The computer 90 is configured to collect information from each band 14-1 to 14-7. To establish a two-dimensional image 92, the computer 90 is configured to juxtapose the information from the different bands 14-1 to 14-7 of the detector 14. To produce a two-dimensional image 90, the actuator 68 remains inactive. The assembly formed by the generator 12 and the detector 14 is immobile with respect to the support 62. The image-taking is similar to that performed by a conventional radiology device in two dimensions or by a device of CBCT type without rotation. The main advantage in implementing the device 10 according to the invention is to reduce the effects of the scattered radiation. In fact, each band 14-1 to 14-7 detects only the radiation contained in the plane of the beam 20 from the corresponding source 16-1 to 16-7 and disregards the scattered radiation outside this plane. More specifically, a band 14-*i* is defined to receive the direct radiation from the corresponding source 16-*i*. The band 14-*i* is completely illuminated by the direct radiation from the corresponding source 16-*i*. Direct radiation is understood to be radiation without scattered radiation. By design of the device, each of the bands is aligned with the beam 20 from the corresponding source. In that way, the pixels of each band receive essentially direct radiation from the corresponding source. Only a very small portion of the scattered radiation from that same source and propagated in the plane of the beam will reach the pixels of that band. Most of the scattered radiation is propagated outside of the plane of the beam and does not therefore reach the pixels of the band concerned. As will be seen later, this large portion of the scattered radiation can be detected by other pixels of the detector situated outside of the band concerned. The bands advantageously have a width smaller than the width of the beam at the detector in order to limit to the maximum the detection of scattered radiation from the beam considered and being propagated away from the plane of the beam. As was seen previously, the beams can slightly overlap. In this situation, it is advantageous to temporarily stagger the emission of immediately adjacent sources, for example as illustrated using FIGS. 5*a* to 5*c*. Still in this situation, the bands of the detector can also overlap. The synchronization of the reading of the bands with the emission of the corresponding sources makes it possible to read all of the bands, each in turn. Implementing the overlapping bands makes it possible to widen the width of each band and therefore to receive a greater signal amplitude. The bands form zones of the detector allocated temporarily to the reading of the stream of photons from each source. The temporary allocation is synchronized with the emission of the sources. In controlling the emission by different sources, a band being able to receive direct radiation other than that originating from the source which is associated with it should be avoided.

It is possible to further enhance the quality of the image. In fact, each band of the detector 14 receives staggered radiation in the very plane of the beam 20 and it is advantageous to correct the measurement made by the detector 14 in each of the bands 14-1 to 14-7 to reduce the part due to the scattered radiation. In each of the bands 14-1 to 14-7, it is possible to estimate this part from measurements done outside of the band considered. In fact, during the emission of the beam 20 opposite the band considered, only this band receives the useful signal from the beam 20 that has passed through the object to be x-rayed. Outside of this band, and outside of other bands opposite beams 20 activated simultaneously only radiation scattered when passing through the object to be x-rayed reaches the detector. By means of measurements performed by the detector outside of the band considered, it is possible to estimate the scattered radiation present in the band itself. The correction of the measurement performed in the band is then possible, by subtraction of the estimation of the scattered radiation from the measured radiation.

Figure 7:
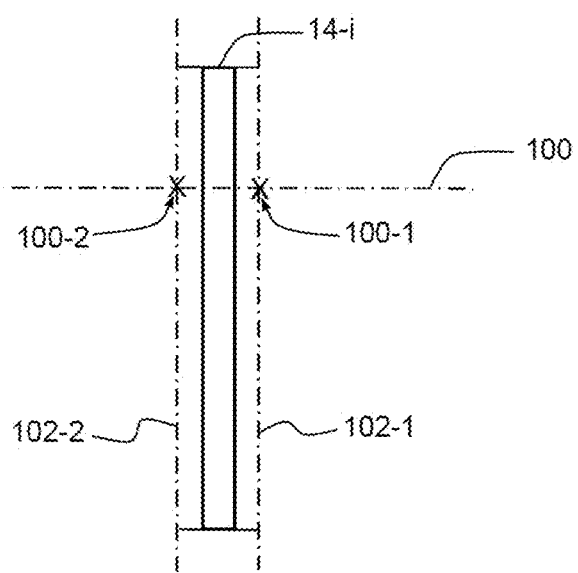
FIG. 7 represents a configuration of the device making it possible to reduce the effects of scattered radiation.

FIG. 7 illustrates several ways of estimating the scattered radiation present in a band illuminated by a beam 20 and referenced 14-*i*. In a first approach, it is possible to consider that the scattered radiation is constant on an axis 100 at right angles to the greatest length of the band 14-*i*. A pixel or a group of pixels 100-1 of the detector 14 situated outside of the band 14-*i* is chosen. The level of radiation scattered inside the band 14-*i* is considered to be equal to the level of the scattered radiation measured by means of the pixel 100-1 during the irradiation of an object to be x-rayed. For all the pixels situated within the band 14-*i* along the axis 100, the value measured by the pixel 100-1 is subtracted from the measurement made.

It is also possible to choose two pixels or two groups of pixels 100-1 and 100-2 both situated outside of the band 14-*i*. The pixels 100-1 and 100-2 are disposed on either side of and equidistant from the band 14-*i*. It is clearly understood that, during the emission of the beam 20, the pixels 100-1 and 100-2 are not illuminated by other beams 20. The estimation of the radiation scattered inside the band 14-*i* is then equal to the average of the measurements in each of the pixels 100-1 and 100-2. These measurements are performed for all the axes at right angles to the greatest length of the band 14-*i*. All the measurement pixels are disposed on axes 102-1 and 102-2 parallel to the greatest length of the band 14-*i*. Since the spatial variation of the scattered radiation is generally slow, it is possible to smooth the measurements done for all the points of 100-1 type on one side and of 100-2 type on the other side along their respective axis 102-1 and 102-2.

The estimation of the level of scattered radiation present in the band 14-*i* can be refined by means of a model of decreasing scattered radiation moving away from the band 14-*i*. The decrease is a function of the distance to the band 14-*i* along the axis 100. This model of decrease can be defined empirically by measurements made from specimen objects of a nature close to the real objects that are desired to be x-rayed. Once the measurements necessary for establishing the model have been done, it is possible to approximate them for example using a polynomial or trigonometric function. From a model retained, it is possible to estimate the level of radiation scattered inside the band 14-*i* by entering into the model measurements made outside of the band, measurements performed during the irradiation of the object to be x-rayed. When an x-ray is being conducted, the measurements made by the pixels 100-1 and 100-2 are introduced into the model retained to estimate the level of radiation scattered inside the band 14-*i*, along the axis 100. As previously, measurements outside of the band 14-*i* are performed on the axes 102-1 and 102-2 in order to make the corrections for all the pixels of the band considered. The use of such a model makes it possible to refine the correction of scattered radiation by individualizing the correction of each of the pixels of the band considered.

The measurement correction that makes it possible to limit the effects of scattered radiation can be implemented in a radiology system that has only a single source 16. In other words, it is advantageous to implement this type of correction in a CT-scanner.

In addition, the computer 90 can be configured to produce a three-dimensional image 94 of an object to be x-rayed situated inside the useful volume 60. To produce a three-dimensional image, it is possible to construct cuts of the object in planes formed by each of the beams 20. These cuts are constructed from information received from the detector by rotating the generator 12 and the detector 14 around the support 62. The three-dimensional image is obtained from the different cuts. To perform this type of reconstruction, it is possible to implement algorithms usually implemented in devices of CT-scanner type. The main advantage in implementing the device 10 according to the invention is then the reduction of the weight to be rotated.

Alternatively, it is possible to construct a three-dimensional image 94 from several two-dimensional images as previously described. Between each two-dimensional image, the generator 12 and the detector 14 are made to rotate about the support 62 by means of the actuator 68. The construction of the three-dimensional image can be performed by implementing an algorithm usually implemented in devices of CBCT type. The main advantage in implementing the device 10 according to the invention is, here, the reduction of the effects of the scattered radiation in each two-dimensional image, which enhances the quality of the three-dimensional image 94.

The invention claimed is:

1. A radiology device comprising an ionizing ray generator and a detector configured to detect the rays emitted by the generator, the generator and the detector being opposite with respect to one another, the device delimiting a useful volume, passed through by the ionizing rays from the generator and received by the detector, wherein the generator comprises several sources distributed along a rectilinear direction and each emitting a beam of ionizing rays that is essentially flat and of fantail form toward the detector extending in a plane perpendicular to the rectilinear direction, in that the sources are disposed so as to irradiate all of the useful volume without translation and so that the beams of ionizing rays are contiguous within the useful volume, further comprising a computer configured to produce a two-dimensional image of an object to be x-rayed situated inside the useful volume without relative movement between the generator and the detector, the computer being configured to collect information from the detector along bands to of the detector, each band being disposed opposite one of the beams, and to establish the two-dimensional image by juxtaposing the information from the different bands of the detector.

2. The device as claimed in claim 1, wherein the computer is configured to produce an estimation of the radiation scattered in each of the bands as a function of radiation measured by the detector outside of the band concerned and to subtract the estimation of the scattered radiation from the measurements performed by the detector in the band concerned.

3. The device as claimed in claim 2, wherein the computer is configured to produce an estimation of the radiation scattered in each of the bands as a function of a model of decreasing scattered radiation moving away from the band concerned.

4. The device as claimed in claim 1, comprising a support capable of bearing an object to be x-rayed and an actuator making it possible to move an assembly formed by the generator and the detector around the support and in that the computer is configured to produce a three-dimensional image of an object to be x-rayed situated in the useful volume from several two-dimensional images produced by moving, between each two-dimensional image, the assembly formed by the generator and the detector around the support.

5. The device as claimed in claim 1, wherein the detector is formed by a flat panel extending on two right-angled axes, a first of the two axes being parallel to the direction in which the sources are distributed, a second of the two axes belonging to a plane in which one of the beams is propagated.

6. The device as claimed in claim 1, wherein the beams are propagated parallel to one another.

7. The device as claimed in claim 1, wherein each source comprises a cold cathode emitting an electron beam by field effect.

8. The device as claimed in claim 7, wherein at least several of the sources have a common vacuum chamber.

9. The device as claimed in claim 1, wherein the generator comprises several series of aligned sources, each series being aligned along a direction and each emitting an essentially flat beam of ionizing rays, the planes of each of the beams being parallel to one another.

10. The device as claimed in claim 9, wherein the directions of each of the series of sources are parallel to one another.

11. A method implementing a device as claimed in claim 1 further comprising successively sequencing the emission of several of the sources.

12. The method as claimed in claim 11, wherein the sources are ordered along their direction and grouped together in subsets each grouping together evenly distributed sources, the subsets being nested in one another, and further comprising controlling the simultaneous emission of the sources of the same subset and in successively sequencing the emission of the different subsets.

13. The method as claimed in claim 11, further comprising spatially and temporarily synchronizing the sources and the detector.

14. The method as claimed in claim 13, further comprising synchronizing the emission of each source with an allocation of the corresponding band of the detector.

15. A method implementing a device as claimed in claim 4, the method further comprising combining the emission of the different sources and the movement of the actuator.

16. The method as claimed in claim 15, further comprising moving the actuator continuously during the emission of the different sources.

* * * * *